(12) United States Patent
Kettl et al.

(10) Patent No.: US 7,367,223 B2
(45) Date of Patent: May 6, 2008

(54) METHOD AND DEVICE FOR ASSESSING THE QUALITY OF A FUEL, IN PARTICULAR A DIESEL OR PETROL FUEL

(75) Inventors: Thomas Kettl, Atting (DE); Hong Zhang, Tegernheim (DE)

(73) Assignee: Siemens Aktiengesellschaft, Munich (DE)

( * ) Notice: Subject to any disclaimer, the term of this patent is extended or adjusted under 35 U.S.C. 154(b) by 30 days.

(21) Appl. No.: 11/548,509

(22) Filed: Oct. 11, 2006

(65) Prior Publication Data
US 2007/0163542 A1 Jul. 19, 2007

(30) Foreign Application Priority Data
Oct. 11, 2005 (DE) .................. 10 2005 048 706

(51) Int. Cl.
*G01M 15/00* (2006.01)
(52) U.S. Cl. ..................................... 73/53.05; 73/118.1
(58) Field of Classification Search ............... 73/53.01, 73/53.05, 112, 113, 115, 116, 117.2, 117.3, 73/118.1, 119 A
See application file for complete search history.

(56) References Cited

U.S. PATENT DOCUMENTS

| 4,905,649 A | 3/1990 | Washino et al. ............ 123/435 |
| 4,920,494 A * | 4/1990 | Abo et al. .................. 701/104 |
| 4,942,848 A | 7/1990 | Terasaka ..................... 123/1 A |
| 5,499,607 A * | 3/1996 | Tomisawa ................... 123/435 |
| 5,537,978 A | 7/1996 | Watanabe et al. ........... 123/435 |
| 2007/0239345 A1* | 10/2007 | Bizub ......................... 701/114 |

FOREIGN PATENT DOCUMENTS

DE 40 19 083 A1 12/1991

* cited by examiner

*Primary Examiner*—Eric S. McCall
(74) *Attorney, Agent, or Firm*—Baker Botts L.L.P.

(57) ABSTRACT

Fuels that are used nowadays can have a different densities or different heating values. Even when filling the fuel tank (7) the quality of the fuel in the fuel tank (7) can change since different fuels are mixed. For example a low density or a low heating value can lead to reduced performance of the internal combustion engine (1). It is therefore proposed that a fuel-specific factor k be determined using a sensor (2, 2a), with which the characteristic of the combustion chamber pressure and/or a lambda value is measured, and using an algorithm. In a further embodiment the operating parameters (injected quantity, start of injection, end of injection, injection pattern, exhaust gas recirculation rate, etc.) are corrected using the factor k.

20 Claims, 2 Drawing Sheets

METHOD AND DEVICE FOR ASSESSING THE QUALITY OF A FUEL, IN PARTICULAR A DIESEL OR PETROL FUEL

PRIORITY

This application claims priority from German Patent Application No. DE 10 2005 048 706.8, which was filed on Oct. 11, 2005, and is incorporated herein by reference in its entirety.

TECHNICAL FIELD

The invention relates to a method and to a device for assessing the quality of a fuel, in particular a diesel or petrol fuel.

BACKGROUND

It is already known that fuels for internal combustion engines, in particular diesel fuels, may have very different densities or heating values. Diesel fuels are usually mixed with additives which may in particular influence the ignition performance, anti-friction and lubricating qualities and the exhaust emissions. A measure of the quality of the ignition performance of diesel fuels is for example the cetane number CZ which is determined on a specially constructed single-cylinder test engine. Comparative fuels, which are compared with the very ignitable n-cetane $C_{16}H_{34}$ and the less ignitable α-methyl naphthalene, can be tested on this test engine. The cetane number is fixed in a range between 0 and 100. A cetane number that is too low pollutes the environment, particularly by forming carbon particulate matter in the case of diesel engines. The cetane number CZ is conventionally between 50 and 55 in Germany.

The cetane number of diesel fuels can differ greatly, it is relatively low in the case of bio-diesel in particular. A further problem lies in the fact that when refuelling, the fuels in the fuel tank are mixed with different qualities. As a result it is very difficult for the motor control unit, for example in the case of a common rail injection system, to control a quantity of fuel to be injected in such a way that optimum combustion results with minimal exhaust gas emissions in particular. Added to this is the fact that in the case of a fuel with a lower density, the energy supplied to the internal combustion engine is less than in the case of a fuel with a higher density. The engine performance is also affected to an undesirable extent as a result. A motor control unit must take all of these factors and the current operating parameters into consideration such that an optimum quantity of fuel to be injected can be calculated in the case of a corresponding torque requirement. With known motor control units these requirements are only insufficiently satisfied, however.

Previously this problem has been solved, in particular in the case of diesel fuels, by fitting an optical sensor in the fuel tank. The optical sensor has the task of inferring the quality from the fuel's opaqueness. However this method is relatively unreliable as individual fuel producers add a dye to the fuel. As a result an objective assessment of the fuel used is rendered considerably more difficult.

SUMMARY

The object of the invention is to directly assess the quality of a fuel in the fuel tank of a motor vehicle during operation of the motor vehicle.

A method for assessing the quality of a fuel being injected into a combustion chamber of an internal combustion engine, with at least one sensor being arranged on the internal combustion engine, may comprise the steps of measuring an operating parameter of the internal combustion engine with the at least one sensor, measuring the pressure characteristic produced during combustion of the fuel in the combustion chamber, and/or measuring at least one corresponding lambda value during a predetermined, constant operating point of the internal combustion engine, evaluating the measured pressure characteristic and/or the at least one lambda value using a stipulated algorithm, and as a result, determining a fuel-specific factor k with which the quality of the fuel is assessed.

An arrangement for assessing the quality of a fuel may comprise a combustion chamber of an internal combustion engine, at least one sensor and a motor control unit, and an evaluation unit operable to process an algorithm for evaluating the sensor signals, wherein the arrangement measures an operating parameter of the internal combustion engine with the at least one sensor, measures the pressure characteristic produced during combustion of the fuel in the combustion chamber, and/or measures at least one corresponding lambda value during a predetermined, constant operating point of the internal combustion engine, evaluates the measured pressure characteristic and/or the at least one lambda value using a stipulated algorithm, and as a result, determines a fuel-specific factor k with which the quality of the fuel is assessed.

The fuel may be a diesel or petrol fuel. The operating parameter can be a combustion chamber pressure and/or a lambda value. The factor k can be supplied to a motor control unit, and the motor control unit may correct the operating parameters for the internal combustion engine using factor k. The operating parameters can be one or more parameters selected from the group consisting of: the fuel pressure, the exhaust gas recirculation rate, the injection pattern, the quantity of fuel to be injected, start of injection, and end of injection. To assess the fuel quality, the pressure characteristic in the combustion chamber during combustion within a predetermined angular range of the crankshaft of the internal combustion engine can be integrated. The density or heating value of the injected fuel can be determined from the integrated pressure characteristic by comparison with stored or calculated quality values of fuels. To assess the quality of the fuel, an ignition delay can be determined, the ignition delay being derived from a delayed increase in the combustion chamber pressure. Furthermore, a lambda probe can be used as a sensor, with a predetermined, constant operating point of the internal combustion engine, a current lambda value can be measured, the current lambda value can be compared with a predetermined, stored or calculated desired lambda value for this operating point, and the difference between the two lambda values can be used as a measure for assessing the quality of the fuel. The constant operating point of the internal combustion engine can be selected such that the desired lambda value is close to the value one. The fuel quality can be assessed at least after filling a fuel tank for the internal combustion engine. The sensor can be constructed as a pressure sensor and may measure the combustion chamber pressure during combustion of the fuel. The sensor can be constructed as a lambda probe, and the lambda probe can be arranged in the exhaust gas system of the internal combustion engine.

BRIEF DESCRIPTION OF THE DRAWINGS

An embodiment of the invention is shown in the schematic drawings and will be described in more detail in the description hereinafter.

DETAILED DESCRIPTION

Figure 1:
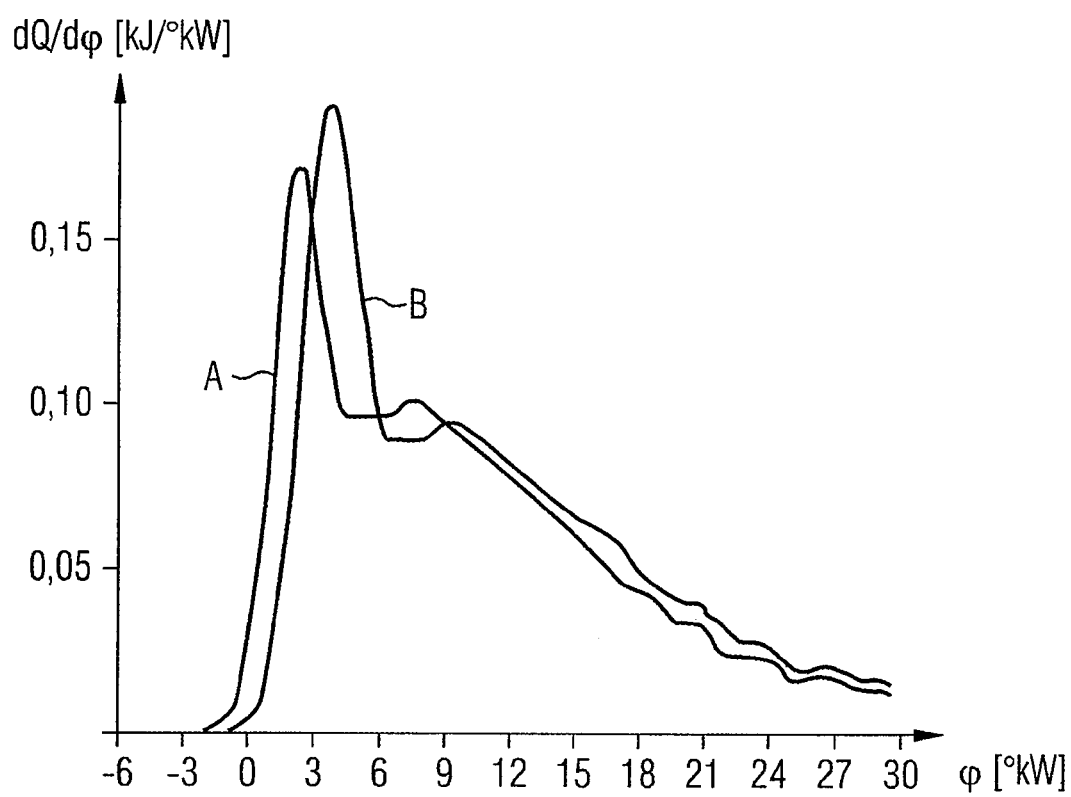
FIG. 1 shows a graph with two fuel curves.

The advantage of the method and the device according to the invention for assessing the quality of a fuel is that the quality of the fuel which is currently in the fuel tank of a vehicle can be assessed with relatively high reliability as well as objectively. This may be achieved for example using a sensor that measures the pressure characteristic, in the combustion chamber of the internal combustion engine, which is produced during combustion of the fuel, and evaluated using a stipulated algorithm. An advantageous alternative solution is seen in the fact that the lambda value measured by a lambda probe is evaluated. The lambda value is measured at a constant operating point of the internal combustion engine and compared with stored desired values. Depending on the fuel quality a different lambda value may result with a constant operating point as different fuels may have different densities or different heating values, so consequently a different combustion picture may result during combustion in the combustion chamber of the internal combustion engine. That the different types or qualities of fuel may be assessed using a single factor is regarded as particularly advantageous, so a comparison of the fuel qualities may consequently be carried out very easily.

A particularly advantageous possibility of development can be seen in that the factor is supplied to a motor control unit. The motor control unit, which already exists in a modern internal combustion engine, can then optimally determine the injection quantity and in the process directly or indirectly control a fuel injector accordingly using the factor and further operating parameters, for example control of the injection instant, control of the period of injection, exhaust gas recirculation, change in multiple injection, rate shaping, etc. For example the start of injection and/or the injection pressure can be changed and the emission targets reached as a result if inferior quality fuel has been found. The quantity of fuel to be injected may also be reduced if the quality of fuel is higher than average.

A particularly simple method for determining the fuel quality consists in the pressure characteristic in the combustion chamber of the internal combustion engine, which occurs during combustion within a predetermined angular range of the crankshaft, being recorded and evaluated. For example the integral may be formed over the pressure curve or a curve corresponding to the pressure characteristic, so the work or quantity of energy obtained therefrom may be determined. Easy assessment of the fuel quality is possible by comparing the determined values with stored or calculated values in order to draw conclusions about the heating value or the density of the injected fuel.

A further advantageous possibility for assessing the quality of the fuel is also seen in the determination of the ignition delay. The ignition delay results from a delayed increase in the combustion chamber pressure. As fuel of different qualities in the combustion chamber produces differently displaced pressure curves, the displacement of the pressure curve, which is an objective measure of the ignition delay, produces a very simple and advantageous possibility for determining the fuel quality.

By assessing the ignition delay conclusions may also be drawn about the fuel assessment, in particular in the case of a diesel fuel, as the instant of the increase in pressure is a measure of the ignition performance of the diesel fuel. The ignition performance of the fuel is determined by what is referred to as the cetane number. The shorter the ignition delay, i.e. the more ignitable the injected fuel is, the higher the cetane number is. The opposite applies in the reverse case for a low cetane number.

A further advantageous possibility for assessing the quality of the fuel also consists in measuring and evaluating a current lambda value for a constant operating point of the internal combustion engine. The lambda value reflects the ratio of air mass admitted to injected quantity of fuel. The lambda value is conventionally measured using a lambda probe which is fitted in the exhaust gas system of the internal combustion engine and measures the residual oxygen in the exhaust gas stream. If for a predetermined, constant operating point of the internal combustion engine different lambda values are measured for different fuels, then fuels of different quality may be deduced.

A fuel quality may be determined particularly reliably if the lambda value is measured for a predetermined, constant operating point and then compared with a corresponding, stored desired lambda value. The comparison produces a measure of the assessment of the fuel quality which is being instantaneously injected into the combustion chamber of the internal combustion engine.

A lambda value of one means that the ratio of the air mass admitted to the injected quantity of fuel attains the value 14.6. At this ratio the lambda probe supplies the most exact measured value, so the operating point for the internal combustion engine during measurement is preferably chosen such that the stored desired lambda value is close to the value one.

Determination and assessment of a fuel is advantageously and preferably carried out when the fuel tank has just been completely or partly re-filled as the process of mixing with the remaining fuel still in the fuel tank results in an average quality for the fuel which is decisive for processing in the motor control unit. According to the invention it is therefore provided that the fuel quality is assessed at least once after filling the fuel tank.

FIG. 1 shows a graph in which two different types of fuel A and B are compared. The two types of fuel A, B differ in that they have a different cetane number CZ. In the case of curve A the cetane number CZ is approximately two units greater than in the case of curve B. The Y-axis of the graph illustrates the specific supply of energy $dQ/d\phi$ [kJ/$^\circ$KW] ($dQ/d\phi$ is the change in energy per crankshaft angle and $^\circ$KW denotes the crankshaft angle in degrees). The X axis indicates the crankshaft angle $\phi$ in degrees. The relative supply of energy corresponds to the increase in pressure in the combustion chamber of the internal combustion engine, caused by the fuel combustion, if, after fuel injection, the crankshaft has exceeded its upper dead centre corresponding to crankshaft angle $\phi=0°$. As may also be gathered from the graph the gradient of curve A in the range 0 to 3° up to its maximum is very steep. Once combustion has ended and as the crankshaft angle increases the pressure in the combustion chamber drops relatively rapidly as the gas mixture in the combustion chamber then cools quickly and the piston moves downward again. The steep gradient of curve A means that the injected fuel is ignited in this region and as a result the combustion chamber pressure rises very rapidly.

Curve B has substantially the same characteristic as curve A but is displaced slightly to the right. Curve B also differs from curve A in that curve B has a greater amplitude. If the integral is formed over the two curves A and B in each case, the supplied energy, which can be taken from the injected fuel in the form of a torque, is obtained. The two curves A, B were determined under identical, constant operating conditions and identical injection quantities of the two fuels A and B, and have already been illustrated in the graph of FIG. 1 in an evaluatable form. The actual pressure characteristic in the combustion chamber of the internal combustion engine has not been explicitly illustrated as it is superimposed by the compressional pressure and therefore cannot be evaluated directly.

To evaluate and assess the quality of different fuels different algorithms may accordingly be used. On the one hand the position of curves A, B in relation to the crankshaft angle $\phi$ and on the other hand the integral over the two curves A, B may be evaluated in the process.

A first possibility for evaluating the two curves A, B consists in drawing a conclusion about the ignition delay of the investigated fuels from the displacement of the two rising regions of curves A, B with the pressure increase since the increase in pressure is a measure of the start of combustion of the injected fuel. A short ignition delay means that the cetane number CZ is high. This is case with curve A. In the case of curve B there is an ignition delay of approximately 2° crankshaft angle. It may therefore be deduced that the cetane number of fuel B is about two units lower than that of fuel A. The two curves A, B thus represent two fuels of differing quality.

A further alternative possibility for determining the quality of a fuel consists in the integral being formed over the two curves A, B in each case. This algorithm provides a particularly reliable result. If, for example, fuel A is injected into a diesel engine in a predetermined quantity and a predetermined operating state, the integral over curve A corresponds to the work obtained, which during combustion may be gathered from the internal combustion engine as a mechanical torque. The two curves A and B are plotted under identical internal combustion engine operating conditions; identical injection quantities in particular were used in the case of both curves. The integral over curve B is greater than the integral over curve A, so the density or heating value of fuel B is greater than that of curve A. This means that with an identical injection quantity the energy supplied to the internal combustion engine turns out to be less as the density decreases, so the internal combustion engine can also only output less power. So the exhaust gas emissions, and in particular the particulate formation, requirements may be satisfied however, according to the invention correction of the injection parameters, for example the quantity of fuel to be injected, the injection pressure, the injection instant, etc. is provided. This correction is necessary in particular if, as a result of filling up, fuels of differing quality are mixed with one another in the fuel tank. It is therefore provided that the fuel quality is checked in particular after filling up. This method may be used in a diesel engine and analogously in a petrol motor.

In practice the reaction illustrated above may be determined very easily using a sensor which is either arranged on the internal combustion engine or in the exhaust gas system. A preferred, very simple embodiment of the device according to the invention is achieved with a pressure sensor which measures the pressure in the combustion chamber of the internal combustion engine.

Figure 2:
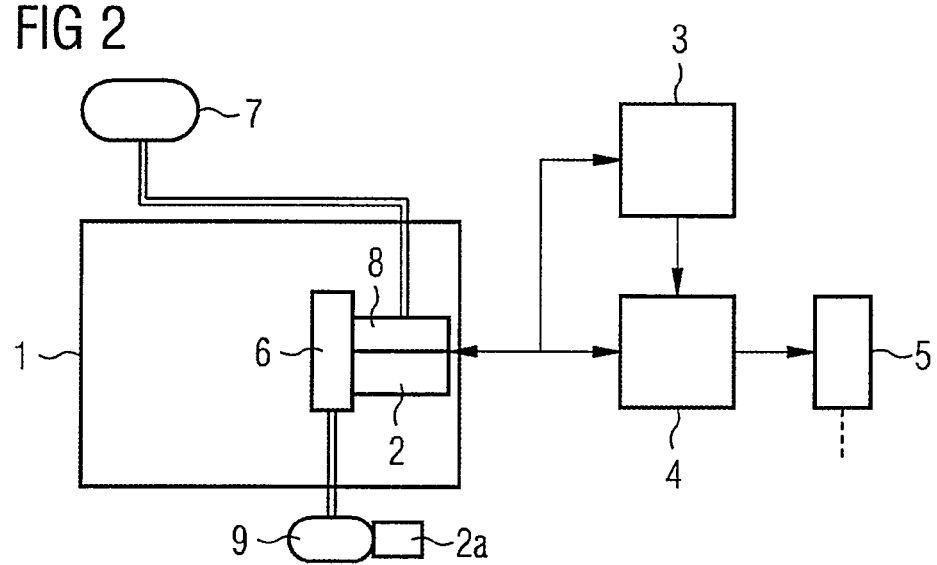
FIG. 2 shows a block diagram with a device according to the invention.

FIG. 2 shows an embodiment in which a device according to the invention is illustrated in the form of a block diagram. FIG. 2 shows an internal combustion engine 1. The internal combustion engine 1 has at least one cylinder with a combustion chamber 6 on which a sensor 2 is arranged. The internal combustion engine 1 is constructed as a diesel or petrol engine with a common rail injection system or any desired fuel supply system. To supply the fuel at least one fuel injector 8 for example, which can be controlled by a motor control unit 4, is used for each cylinder or combustion chamber 6. The fuel injector 8 is also connected to a fuel tank 7 in which the fuel to be assessed is filled.

In the first embodiment of the invention a pressure sensor 2 is used which is constructed for recording the pressure of the combustion chamber. The pressure sensor 2 on the one hand supplies its measured values to the motor control unit 4 and on the other hand to a device 3 for evaluating this measured data. Using the stipulated algorithm the device 3 determines a factor k which is a measure of the quality of the instantaneously injected fuel. The factor k is transmitted to the motor control unit 4, so in addition to the operating parameters already measured and processed, for example the injection pressure, the injection instant, the period of injection, the exhaust gas recirculation, etc., the motor control unit 4 may also correct the quantity of fuel to be injected in accordance with factor k. Factor k can in this case be processed in any desired function. The quality of the fuel is determined at a predetermined, constant operating point of the internal combustion engine 1. It is consequently possible to easily read factor k off a table, for example by way of stored values for comparable fuels. The integral over the curve obtained, corresponding to the graph in FIG. 1, which is formed from the measured values during combustion of the fuel, is preferably determined as the algorithm. The integrated curve is therefore a measure of the work which can be obtained with the predetermined injected quantity of fuel. The lower the work obtained, the lower the density or heating value of the fuel. This means that compared with a higher-quality fuel the quantity of fuel to be injected or the exhaust gas recirculation rate, etc. for example has to be increased by factor k.

As already mentioned the ignition delay may alternatively or additionally be used to assess the injected fuel since a shorter ignition delay may for example be seen for a fuel with a higher cetane number.

A further alternative possibility for assessing the quality of a fuel may also be seen by way of a lambda probe 2a. The lambda probe 2a is fitted in an exhaust gas system 9 of the internal combustion engine and measures the residual oxygen in the exhaust gas. In a similar manner, as described above, different fuel qualities also produce different lambda values if the measurements are made using identical injection parameters and with identical internal combustion engine operating conditions in each case. The lambda probe 2a has its highest degree of accuracy when the lambda value is close to the value one. According to the invention the lambda value is therefore measured under operating conditions in which the lambda value is close to the value one. With a higher lambda value, i.e. with a lean fuel-air mixture, the residual oxygen content in the exhaust gas is lower. In the opposite case, the oxygen content is analogously higher if the fuel-air mixture is rich and therefore the lambda value is greater than one. This method may be used in diesel and petrol engines.

Figure 3:
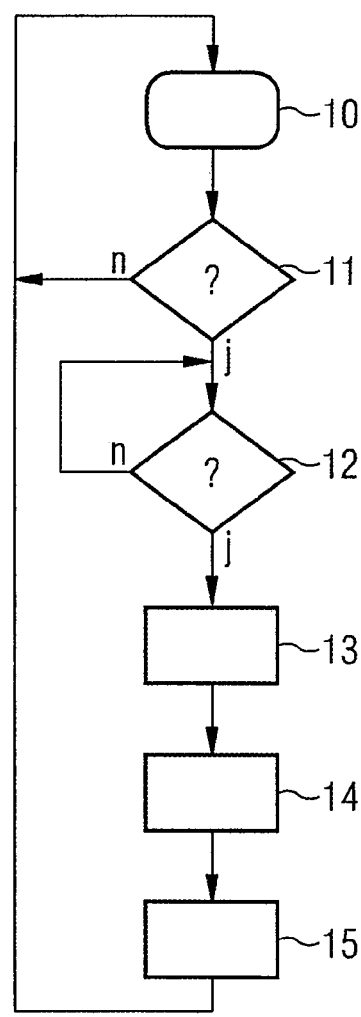
FIG. 3 shows a flow diagram that may be used to assess the fuel quality.

FIG. 3 shows a flow diagram with which a fuel may be assessed. The program starts in position 10. The engine is started and a check is then carried out in position 11 as to whether the fuel tank has been refilled. The simplest way of carrying out this check is to query the level indicator. If this is not the case, at n the program jumps back to position 10.

If, on the other hand, the fuel tank has been at least partially filled at j, a check is carried out in position 12 as to whether a predetermined, constant operating point of the internal combustion engine 1 has been attained. If this is not the case, at n the programme jumps back to check routine 12 again. Otherwise there is a sensor measurement at j in position 13, which measurement may be carried out using the pressure sensor 2 or the lambda probe 2*a* for example. The measurement may optionally be repeated several times and a corresponding average formed to obtain a more reliable result. Evaluation takes place in position 14 using the stipulated algorithm. As a result a factor k is determined which is stored in position 15. The factor k which has been found is then supplied to the motor control unit 4 to make a corresponding adjustment for the quantity of fuel to be injected. In the process parameters, such as the injection pressure, the injection instant, the injection period, the exhaust gas recirculation, etc. may be adjusted. For example the injection time or injection period may be extended in the case of an insufficient heating value. The supply of fuel may thus be optimised very easily with respect to a desired torque requirement and/or observance of exhaust gas emissions.

What is claimed is:

1. A method for assessing the quality of a fuel being injected into a combustion chamber of an internal combustion engine, with at least one sensor being arranged on the internal combustion engine, the method comprising the steps of:
    measuring an operating parameter of the internal combustion engine with the at least one sensor,
    measuring the pressure characteristic produced during combustion of the fuel in the combustion chamber and/or measuring at least one corresponding lambda value during a predetermined, constant operating point of the internal combustion engine,
    evaluating the measured pressure characteristic and/or the at least one lambda value using a stipulated algorithm, and
    as a result, determining a fuel-specific factor k with which the quality of the fuel is assessed.

2. The method according to claim 1, wherein the fuel is a diesel or petrol fuel.

3. The method according to claim 1, wherein the operating parameter is a combustion chamber pressure and/or a lambda value.

4. The method according to claim 1, wherein to assess the quality of the fuel an ignition delay is determined, the ignition delay being derived from a delayed increase in the combustion chamber pressure.

5. The method according to claim 1, comprising the steps:
    using a lambda probe as a sensor,
    with a predetermined, constant operating point of the internal combustion engine, measuring a current lambda value,
    comparing the current lambda value with a predetermined, stored or calculated desired lambda value for this operating point, and
    using the difference between the two lambda values as a measure for assessing the quality of the fuel.

6. The method according to claim 1, wherein the fuel quality is assessed at least after filling a fuel tank for the internal combustion engine.

7. The method according to claim 1, wherein the factor k is supplied to a motor control unit, and the motor control unit corrects the operating parameters for the internal combustion engine using factor k.

8. The method according to claim 7, wherein the operating parameters are one or more parameters selected from the group consisting of: the fuel pressure, the exhaust gas recirculation rate, the injection pattern, the quantity of fuel to be injected, start of injection, and end of injection.

9. The method according to claim 1, wherein to assess the fuel quality the pressure characteristic in the combustion chamber during combustion within a predetermined angular range of the crankshaft of the internal combustion engine is integrated.

10. The method according to claim 9, wherein the density or heating value of the injected fuel is determined from the integrated pressure characteristic by comparison with stored or calculated quality values of fuels.

11. The method according to claim 9, wherein the constant operating point of the internal combustion engine is selected such that the desired lambda value is close to the value one.

12. An arrangement for assessing the quality of a fuel, in particular a diesel or petrol fuel, comprising a combustion chamber of an internal combustion engine, at least one sensor and a motor control unit, and an evaluation unit operable to process an algorithm for evaluating the sensor signals, wherein the arrangement measures an operating parameter of the internal combustion engine with the at least one sensor, measures the pressure characteristic produced during combustion of the fuel in the combustion chamber, and/or measures at least one corresponding lambda value during a predetermined, constant operating point of the internal combustion engine, evaluates the measured pressure characteristic and/or the at least one lambda value using a stipulated algorithm, and as a result, determines a fuel-specific factor k with which the quality of the fuel is assessed.

13. The arrangement according to claim 12, wherein the sensor is constructed as a pressure sensor and measures the combustion chamber pressure during combustion of the fuel.

14. The arrangement according to claim 12, wherein the sensor is constructed as a lambda probe, and the lambda probe is arranged in the exhaust gas system of the internal combustion engine.

15. The arrangement according to claim 12, wherein to assess the quality of the fuel an ignition delay is determined, the ignition delay being derived from a delayed increase in the combustion chamber pressure.

16. The arrangement according to claim 12, wherein the arrangement assesses the fuel quality at least after filling a fuel tank for the internal combustion engine.

17. The arrangement according to claim 12, wherein the factor k is supplied to a motor control unit, and the motor control unit corrects the operating parameters for the internal combustion engine using factor k.

18. The arrangement according to claim 17, wherein the operating parameters are one or more parameters selected from the group consisting of: the fuel pressure, the exhaust gas recirculation rate, the injection pattern, the quantity of fuel to be injected, start of injection, and end of injection.

19. The arrangement according to claim 12, wherein to assess the fuel quality the pressure characteristic in the combustion chamber during combustion within a predetermined angular range of the crankshaft of the internal combustion engine is integrated.

20. The arrangement according to claim 19, wherein the density or heating value of the injected fuel is determined from the integrated pressure characteristic by comparison with stored or calculated quality values of fuels.

* * * * *